(12) United States Patent
Hilvert et al.

(10) Patent No.: US 6,783,027 B2
(45) Date of Patent: Aug. 31, 2004

(54) METERED-DOSE UNDERARM PRODUCT AND PACKAGE

(75) Inventors: Jennifer Elaine Hilvert, Cincinnati, OH (US); Theresa Louise Johnson, Batesville, IN (US); Kenneth Michael Schroeder, Erlanger, KY (US); Scott Edward Smith, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/146,001
(22) Filed: May 15, 2002

(65) Prior Publication Data
US 2003/0213818 A1 Nov. 20, 2003

(51) Int. Cl.7 .......................... B65D 83/14; B65D 83/20
(52) U.S. Cl. ........................................ 222/1; 222/402.2
(58) Field of Search ................................. 222/402.2, 1

(56) References Cited

U.S. PATENT DOCUMENTS 2,693,983 A * 11/1954 Howell .................... 222/402.2
2,746,796 A *  5/1956 Germain .................. 222/402.2
4,431,120 A *  2/1984 Burger ................... 222/402.18

* cited by examiner

Primary Examiner—Kenneth Bomberg
(74) Attorney, Agent, or Firm—Jack L. Oney; Vlad Vitenberg

(57) ABSTRACT

An underarm product and a spray package having a metered-dose valve assembly. The underarm product is contained and pressurized inside of the package. The underarm product being in the form of a liquid or emulsion. The underarm product is an antiperspirant or a deodorant. The underarm product contains a solubilized and/or non-solubilized propellant.

9 Claims, 2 Drawing Sheets

METERED-DOSE UNDERARM PRODUCT AND PACKAGE

TECHNICAL FIELD

The present invention relates to a pressurized underarm product and package having a metered-dose valve assembly capable of delivery a reduced amount of product while achieving improved consumer acceptance.

BACKGROUND OF THE INVENTION

The consumer products industry provides the world's consumers with a wide variety of products that are designed to meet consumer's needs. These personal care products are designed to not only meet the functional needs of consumers but also create a usage experience that is pleasurable. The number and variety of products that are available to today's consumers is vast and spans a broad range of functional design, aesthetic design, and intended use. These products can be grouped in numerous ways. For example, products can be grouped by function (cleansing, odor prevention, treatment, cosmetic enhancement, sensory experience, etc.), form (sprays, creams, lotions, wipes, bars, lathering soaps, etc.), and/or intended use (for hair, teeth, facial skin, legs, underarms, whole body). When considering the function, form and intended use, it is important to consider the package needed. The type of package and the function of this package must work in a synchronized fashion with the product. Pressurized packages like hairspray, deodorant; cooking oils, paint and cleansers have all been accepted when delivered as sprays, mousses or gels.

Currently marketed underarm products (e.g., antiperspirants, deodorants) typically are sold in the form of a stick in a canister, a gel in a canister, or a powdered active (suspended or dissolved) in a pressurized package. Different than these existing products forms, it is the intent of the present invention to place a liquid or emulsion underarm product in a pressurized package for a variety of reasons including, but not limited to, providing a substantially single-phase product which is more visually attractive to the consumer.

In applying the proper amount of antiperspirant product to a target surface (e.g., consumer's underarm), the amount of antiperspirant active that will ultimately be deposited must be considered. It is commonly desired to deliver from about 0.075 grams to about 0.5 grams of antiperspirant active to the target surface, regardless of the product form. In considering the use of spray packages (e.g., pressurized aerosol packages), it has been discovered that a typical consumer sprays the product (i.e., actuates the spray package) on average for 2 seconds, regardless of the amount of product being delivered because the consumer usually doesn't see the amount of product that is ultimately delivered to their underarm. Therefore, historically when designing a package to spray an antiperspirant product, one skilled in the art must first adhere to this overriding consumer behavior of continuously spraying for 2 seconds. All other design aspects would then follow.

It has been discovered that liquid or emulsion underarm products can provide a thinner and more continuous film layer that coats the underarm better than powders or gels. Therefore, it has also been discovered that a smaller amount of product may be needed when spraying a liquid or emulsion to achieve similar product efficacy results. Furthermore, spraying too much of a liquid or emulsion product may result in a wet/runny cosmetic feel, while spraying too little of a liquid or emulsion product may result in a unacceptable efficacy results. Historically, to spray a smaller amount of product, two design techniques would be used separately or jointly. First, the package would be designed to have smaller orifice sizes within its flow channels, however, smaller orifices are more prone to clogging (especially with the presence of impurities within the product) and they create smaller particles of the product, which have undesirable spray properties (i.e., small particles don't travel as far as larger particles). Secondly, the internal pressure of the product within the package would be reduced, however, this would require reformulating the product composition.

What is needed is a package capable of dispensing a liquid or emulsion underarm product that overcomes the long-standing consumer behavior of spraying for 2 seconds and also provides a robust solution that is better than the problematic techniques of reducing flow channel orifice size or changing internal package pressure. It has been discovered that a spray package having a metered-dose type valve system provides these desired benefits. Additionally and surprisingly, it has been discovered that by positively impacting the particle size distribution of the sprayed product, a metered-dose type valve system (1) increases the amount of product that is ultimately deposited on the target surface (i.e., product deposition) and (2) decreases the amount of sprayed particles that becomes air borne (i.e., gassiness) and thus susceptible to being inhaled by the consumer or deposited in the environment. These discoveries will be discussed in greater detail.

SUMMARY OF THE INVENTION

The present invention provides an underarm product and a spray package. The spray package has a metered-dose valve assembly. The underarm product is contained and pressurized inside of the package. The underarm product being in the form of a liquid or emulsion. The underarm product is an antiperspirant or a deodorant. The underarm product contains a solubilized and/or non-solubilized propellant.

Other advantages and novel features of the present invention will become apparent to those skilled in the art from the following detailed description, which simply illustrates various modes contemplated for carrying out the invention. As will be realized, the invention is capable of other different obvious aspects, all without departing from the invention. Accordingly, the drawings and descriptions are illustrative in nature and not restrictive.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify like elements and wherein:

DETAILED DESCRIPTION OF THE INVENTION

Reference will now be made in detail to various exemplary embodiments of the invention, several of which are also illustrated in the accompanying drawings, wherein like numerals indicate the same elements throughout the views, and numbers with the same final two digits indicate corresponding elements among embodiments.

Figure 1:
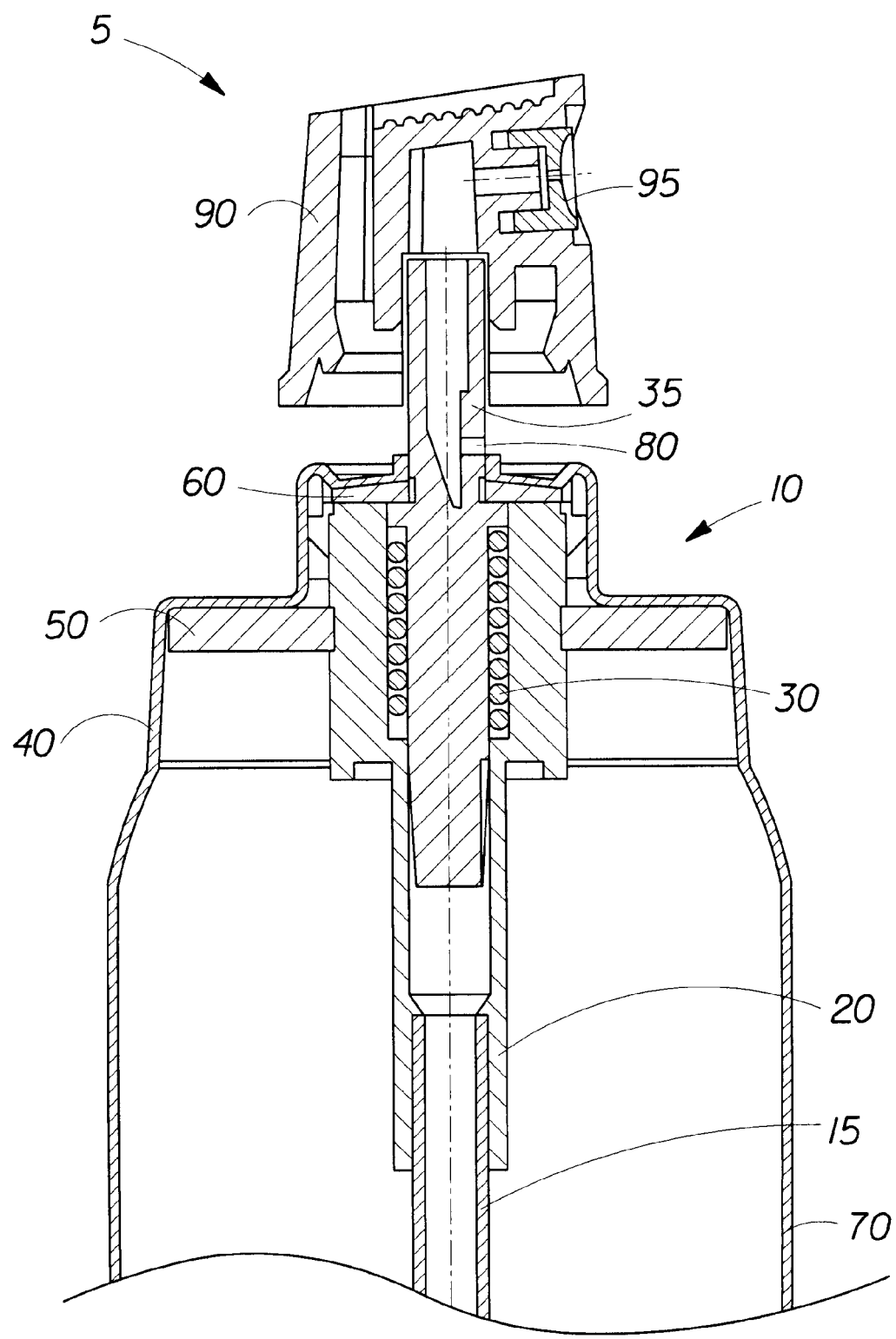
FIG. 1 is a cross-sectional view of a spray package having a metered-dose valve assembly and a container in accordance with the present invention.

FIG. 1 depicts a non-limiting exemplary embodiment of a spray package 5 having a metered-dose valve assembly 10. Metered-dose valve assembly 10 has a dip tube 15 which provides a flow channel for delivery of a product (e.g., underarm product) to the valve housing 20. Valve housing 20 provides a volumetric chamber for product containment and also has a mechanical assembly area for supporting the spring 30 and stem 35. Spring 30 and stem 35 may be constructed as individual or combined parts. Spring 30 provides an energy constant to return the stem 35 to a closed/sealed position. Stem 35 provides a connection between valve housing 20 and actuator 90. In the metered valve, the stem 35 provides the function of shut off of the flow of product from the dip tube 15 and the valve housing 20. This shut off operation is achieved by designing stem 35 such that its bottom end impacts the top of dip tube 15 or bottom end of the valve housing 20 at the time of or before the stem orifice 80 opens. By designing the opening and shut off functions in this manner, only the product contained within the valve housing 20 is dispensed. Ferrule 40 mechanical fastens the metered-dose valve assembly 10 to container body 70. Valve gasket 50 provides a seal between ferrule 40 and container body 70. Stem gasket 60 provides a seal between valve housing 20 and ferrule 40, as well as a seal between stem orifice 80 and the flow of the product. Each of the gaskets in the Metered-dose valve assembly 10 may be compressed to conform between surfaces. For valve gasket 40, compression minimizes any potential leakage between ferrule 40 and container body 70. For stem gasket 60, compression minimizes any potential leakage between valve housing 20 and the environments or to stem orifice 80. Stem orifice 80 provides a flow channel from valve housing 20 to actuator 90.

Figure 2:
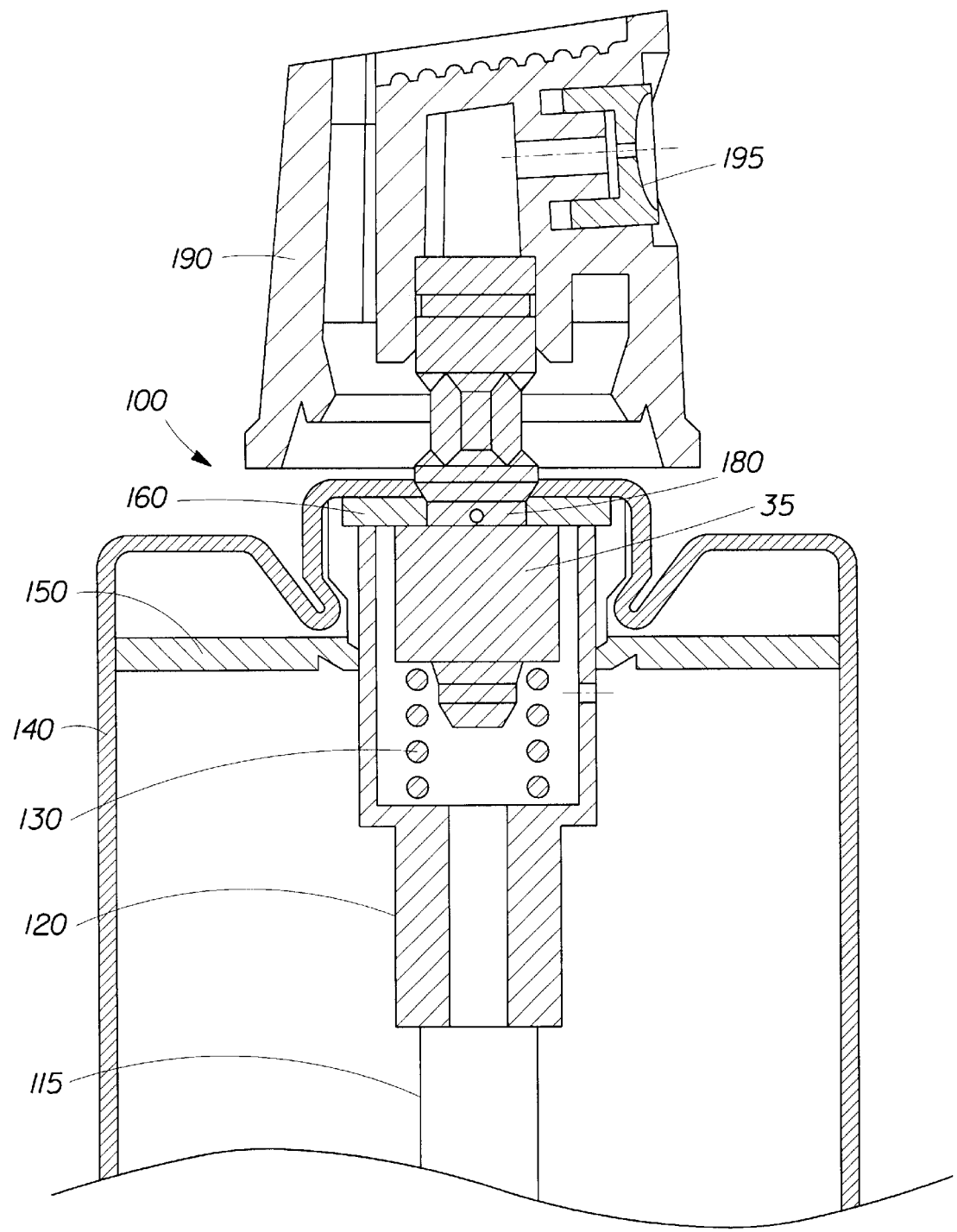
FIG. 2 is a cross-sectional view of a continuous-flow valve assembly for a spray package that is commonly found in the prior art.

FIG. 2 depicts an example embodiment of a continuous-flow valve assembly 110. Continuous-flow valve assembly 110 has a dip tube 115 which provides a flow channel for delivery of a product (e.g., underarm product) to the valve housing 120. Valve housing 120 has a mechanical assembly area for supporting the spring 30 and stem 35. Spring 30 and stem 35 may be constructed as individual or combined parts. Spring 30 provides an energy constant to return the stem 35 to a closed/sealed position. Stem orifice 180 provides a flow channel from valve housing 20 to actuator 190. Depressing of actuator 190 causes product to be sprayed in a continuous fashion from the package. Exit channel 195 provides an exit flow channel for the flow of product just before it is sprayed.

To appreciate the present invention, one should recognize that the metered-dose valve assembly 10 only allows for a metered dose such that the amount of product delivered is controlled (e.g., controlled by the volume of the valve housing 20). In contrast, the continuous-flow valve assembly 100 does not control the amount dosed, rather the amount of product delivered is dependent upon the duration of time that the consumer depresses actuator 190. It should also be appreciated by one skilled in the art that the design of metered-dose valve assembly 10 may be altered in a variety of ways but that the important characteristic is that the valve assembly used must deliver controlled volumes of product (i.e., not a continuous spray).

Additionally and surprisingly, it has been discovered that by positively impacting the particle size distribution of the sprayed product, a metered-dose type valve system (1) increases the amount of product that is ultimately deposited on the target surface (i.e., product deposition) and (2) decreases the amount of sprayed particles that becomes air borne (i.e., gassiness) and thus susceptible to being inhaled by the consumer or deposited in the environment.

As previously mentioned, it is desirable to spray a smaller amount of a liquid or emulsion product because of its improved deposition characteristics as compared to sprayed powders. It has been discovered and appreciated that a metered-dose valve assembly 10 is capable of delivering a smaller amount of product as compared to a continuous-flow valve assembly 100 having similar orifice sizes. While the valves used in the experiment below do not have identical orifice sizes, it should be recognized that (1) increasing orifice size will increase spray rate [compare sample A to B] and (2) a continuous-flow valve assembly 100 has a higher spray rate than a metered-dosed valve assembly 10 [compare sample B to C, despite C being smaller in orifice size]. Wishing not to be bound by theory, it is believed that the continuous-flow valve assembly 100 experiences a continued back pressure from the constant pressure within the container body until the actuator is released, whereas, the metered-dosed valve assembly 10 has minimal back pressure since the product has already been volumetrically measured and separated from the product remaining in the container body. It is further believed that the back pressure in the continuous-flow valve assembly 100 causes the later sprayed particles to be kinetically energized resulting in smaller particles by either additional bombardment or additional aerodynamic resistance causing shearing.

| Sample | Valve Type | Stem Orifice | Tail | Dip Tube | Actuator | Spray Rate (g/s) |
|---|---|---|---|---|---|---|
| A | Continuous | 0.013" | 0.008" | 0.122" | 0.013" | 0.25 |
| B | Continuous | 0.016" | 0.016" | 0.122" | 0.013" | 0.49 |
| C | Metered | 0.020" | 0.045" | 0.045" | 0.013" | 0.25 |

These discovered differences in spray characteristics have also been found to impact the particle size distribution (PSD) of the product being sprayed. For example, the commonly measured Dv(10) value is a measure of the average size of the particles in the lowest ten percent of the volume of the sprayed product. Similarly, Dv(50) is a measure of the average particle size of the fifty percentile of the sprayed product and Dv(90)) is a measure of the average particle size of the ninety percentile of the volume of the sprayed product. It is appreciated that when the Dv(10) value increases, the gassiness or dustiness (defined herein as sprayed particles that fail to reach the target surface and become air borne and more likely to be inhaled by the consumer or deposited on a non-targeted surface) of the sprayed product decreases. Reducing the gassiness inherently increases the potential for more product to be deposited on the target surface (i.e., product deposition). It is also currently believed that increasing the overall PSD (e.g., Dv(10), Dv(50) and Dv(90)) of the sprayed product is desirable to improving product deposition.

| Valve Type | Stem Orifice | Tail | Dip Tube | Actuator | SpRt (g/s) | Dv(10) | Dv(50) | Dv(90) |
|---|---|---|---|---|---|---|---|---|
| Continuous | 0.013" | 0.008" | 0.122" | 0.013" | 0.25 | 14.33 | 43.82 | 86.04 |
| Metered | 0.020" | 0.045" | 0.045" | 0.013" | 0.25 | 19.74 | 52.86 | 115.6 |

The following are two non-limiting examples of a metered-dose valve assembly that have proven successful in practicing the present invention:

1. Manufactured by: Seaquist
   Part #: MV20–25
   25 MCL Metered Body
   0.020" Stem
   Buna-P Diaphragm
   0.021" Spring
   Buna-P Liner
   Ferrule: Un-Anodized
   Capillary 0.045" I.D. Dip Tube, Cut to 4" Length
2. Manufactured by: Seaquist
   Part#: MV20–185
   185 MCL Metered Body
   0.020" Stem
   Buna-P Diaphragm
   0.021" Spring
   Buna-P Liner
   Ferrule: Un-Anodized
   Capillary 0.045" I.D. Dip Tube, Cut to 4" Length

Liquid Aerosol Antiperspirants and Deodorants

Aerosol antiperspirant or deodorant can generally be divided into two classifications, liquid products and powder suspension products. These two classifications differ based on the physical state of the antiperspirant or deodorant active. Suspension products employ an active that is a powder, which is suspended in a liquid carrier. The powdered active can provide a dry feeling efficacious product but generally creates a significant amount of white residue on skin and/or clothes that is a consumer negative.

In the liquid antiperspirant or deodorant products of the present invention, the active is dissolved in a solvent. The solubilized active is then either dispersed or dissolved in a carrier liquid. Products in which the solubilized active is dispersed in the carrier liquid are generally referred to as a liquid emulsion product. Products in which the solubilized active is dissolved in the carrier liquid are generally referred to as a single-phase liquid product. It is the intent of this invention to provide a package that delivers a metered dose for both liquid emulsion and single phase liquid antiperspirant and deodorant products.

Propellant

The aerosol antiperspirant and deodorant compositions of the present invention comprise a propellant that creates enough pressure to force the product from the canister for application. Products of the instant invention typically have an internal package pressure from about 10 PSIG to about 80 PSIG depending on the application method. Pressure level may be controlled by the type and level of propellant used. Propellant may be solubilized or non-solubilized (e.g., emulsified in the product by shaking, or included in the headspace of the package) within the product composition.

The propellant component of the aerosol antiperspirant compositions of the present invention may contain any known propellant that is compatible with the formulation and package of choice. Preferred propellants are generally in the form of liquefied gases when formulated into the antiperspirant compositions and include dimethylether, 1,1 difluoroethane, 1,1,1,2 tetrafluoro ethane, butane, isobutane, propane, isopentane, pentane or combinations thereof. Dimethyl ether or combination of dimethylether and hydrocarbon propellants are preferred for products that are a single-phase, liquid antiperspirant or deodorant products. Hydrocarbon propellants such as butane, isobutane, propane, isopentane, pentane are preferred for products that are liquid emulsion antiperspirant or deodorant products. The total propellant concentration in the anhydrous antiperspirant compositions of the present invention ranges from about 5% to about 99%, more typically from about 15% to about 90%, even more preferably from about 20% to about 70%, by weight of the composition. Other suitable propellants include nitrous oxide, carbon dioxide, and halogenated hydrocarbons such as triclorofluoromethane, diclorodifluoromethane, diclorotetrafluoroethane trichlorotrifluoroethane, trichlorotetrafluoroethane, and monochlorodifluoromethane, and combinations thereof.

Antiperspirant and Deodorant Actives

The aerosol antiperspirant and deodorant compositions of the present invention comprise a antiperspirant active and/or deodorant active suitable for application to human skin. The concentration of antiperspirant and/or deodorant active in the composition should be sufficient to provide the finished antiperspirant product with the desired perspiration wetness and/or odor control benefit.

Antiperspirant active concentrations in the aerosol antiperspirant compositions of the present invention preferably range from about 0.1% to about 26%, more preferably from about 1% to about 20%, even more preferably from about 2% to about 10%, by weight of the composition. All such weight percentages are calculated on an anhydrous metal salt basis exclusive of water and any complexing or buffering agent such as glycine, glycine salts, or other complexing or buffering agent.

The antiperspirant active for use in the antiperspirant compositions of the present invention includes any compound, composition or other material having antiperspirant activity. Preferred antiperspirant actives include astringent metallic salts, especially the inorganic and organic salts of aluminum, zirconium and zinc, as well as mixtures thereof. Particularly preferred are salts such as aluminum halides, aluminum chlorohydrate, aluminum hydroxyhalides, zirconyl oxyhalides, zirconyl hydroxyhalides, and mixtures thereof. Aluminum salts are most preferred for non-contact pressurized compositions.

Preferred aluminum salts for use in the antiperspirant compositions include those that conform to the formula:

$$Al_2(OH)_aCl_b \cdot x\, H_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide" wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, and Gosling et al., issued Nov. 16, 1982, all of which are incorporated herein by reference. Mixtures of aluminum salts are described in British Patent Specification 1,347,950, Shin et al., published Feb. 27, 1974.

Zirconium salts for use in the antiperspirant compositions, especially in pressurized contact forms, include those, which conform to the formula:

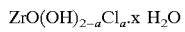

$$ZrO(OH)_{2-a}Cl_a \cdot x\ H_2O$$

wherein a is any number having a value of from 0 to about 2; x is from about 1 to about 7; and wherein a and x may both have non-integer values. Preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978. Zirconium salts are preferably used in products that deliver the product via an application device that is rubbed on the skin.

Preferred antiperspirant actives for use in the compositions include aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum sulfate buffered and combinations thereof.

The deodorant compositions of the present invention comprise a deodorant active at concentrations ranging from about 0.001% to about 50%, preferably from about 0.01% to about 20%, more preferably from about 0.1% to about 10%, even more prefer-ably from about 0.1% to about 5%, by weight of the composition. These deodorant actives include any known or otherwise safe and effective deodorant active or fragrance suitable for topical application to human skin. Unless otherwise specified, the term "deodorant active" as used herein refers generally to topical materials which can prevent or eliminate or cover or mask malodors resulting from perspiration.

Deodorant actives suitable for use in the deodorant composition of the present invention include antimicrobial agents (e.g., bacteriocides, fungicides), malodor absorbing materials, fragrances or combinations thereof. Preferred deodorant actives are antimicrobial agents, non-limiting examples of which include cetyltrimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammoniumchloride, 2,4,4'-trichlorio-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Other deodorant actives include odor-absorbing materials such as carbonate and bicarbonate salts, including alkali metal carbonates and bicarbonates, ammonium and tetraalkylammonium Preferred are sodium and potassium salts of such odor-absorbing materials.

Other deodorant actives include fragrances that are known for or are otherwise effective in masking malodor associated with perspiration, or which other-wise provides the composition with the desired perfumed aroma. These fragrances include any perfume or perfume chemical suitable for topical application to the skin. The concentration of the fragrance in the deodorant composition should be effective to provide the desired aroma characteristics or to mask malodor, wherein the malodor is inherently associated with the composition itself or is associated with malodor development from human perspiration Fragrances are made by those skilled in the art in a wide variety of fragrances and strengths. Typical fragrances are described in Arctander, Perfume and Flavour Chemicals (Aroma Chemicals), Vol. I and II (1969);and Arctander, Perfume and Flavour Materials of Natu-ral Origin (1960). U.S. Pat. Nos. 4,322,308 and 4,304,679, both incorporated herein by reference, disclose fragrance components as generally including, but are not limited to, volatile phenolic substances (such as isoamyl salicylate, benzyl salicylate, and thyme oil red); essence oils (such as geranium oil, patchouli oil, and petitgrain oil); citrus oils; extracts and resins; "synthetic" oils (such as Bergarnot 37 and 430, Geranium 76 and Pomeransol 314); aldehydes and ketones (such as B-methylnaphthyl ketone, p-t-butyl-A-methyl hydrocinnamic aldehyde and p-t-amyl cyclohexanone); polycyclic compounds (such as coumarin and naphthyl methyl ether); esters (such as diethyl phthalate, phenylethyl phenylace-tate, non-anolide-1:4). Fragrances also include esters and essential oils derived from floral materials and fruits, cit-rus oils, absolutes, aldehydes, resinoides, musk and other animal notes (e.g., natural isolates of civet, castoreum and musk), balsamic, etc. and alcohols (such as dimyrcetol, phenylethyl alcohol and tetrahydromuguol). Examples of such components useful in fragrances herein in-clude decyl aldehyde, undecyl aldehyde, undecylenic al-dehyde, lauric aldehyde, amyl cinnamic aldehyde, ethylmethyl phenyl glycidate, methyl nonyl acetaldehyde, myristic aldehyde, nonalactone, nonyl aldehyde, octyl al-dehyde, undecalactone, hexyl cinnamic aldehyde, ben-zaldehyde, vanillin, heliotropine, camphor, para-hydroxyphenolbutanone, 6-acetyl 1,1,3,4,4,6 hexamethyl tetrahydronaphthalene, alpha-methyl ionone, gamma-methyl ion-one, and amyl-cyclohexanone and mixtures of these components.

Some non-limiting examples of other suitable odor masking fragrances which are described in U.S. Pat. Nos. 5,554, 588, 4,278,658, 5,501,805, and EP Patent Application 684 037 A1, all of which are incorporated herein by reference in their entirety. Preferred odor masking fragrances are those which have a Deodorant Value of at least about 0.25, more preferably from about 0.25 to about 3.5, even more preferably from about 0.9 to about 3.5, as measured by the Deodorant Value Test described in EP Patent Application 684 037 A1. The fragrance for use herein may also contain solubilizers, diluents, or solvents which are well known in the art. Such materials are described in Arctander, Perfume and Flavour Chemicals (Aroma Chemicals), Vol. I and II (1969). These materials typically include small amounts of dipropylene glycol, diethylene glycol, C1–C6 alcohols, and/or benzyl alcohol.

Active Solvent

The liquid aerosol antiperspirant and deodorant products of the current invention will include a liquid capable of dissolving the antiperspirant and/or deodorant active that is suitable for application to the human body. Choice of solvent is dependent on choice of antiperspirant and or deodorant active. Preferred solvents include water, ethanol, and liquid polyols.

For liquid antiperspirant products of the present invention the preferred solvent is a liquid polyol The most preferred liquid polyols for use in the antiperspirant composition of the present invention are selected to have at least 3 carbon atoms and adjacent hydroxy-substituted carbon atoms at the α and β positions of the liquid polyol that conform to the formula:

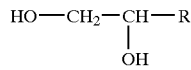

wherein R is an amide, ester, alkyl, ether or silicone-containing moiety, each moiety containing at least 1 carbon atom. The R group is preferably an alkyl or ether group, more preferably an alkyl group having from about 1 to about 10 carbon atoms, more preferably from about 2 to about 6 carbon atoms. The liquid polyols preferably have either 2 or 3 hydroxyl groups in total.

The R group on the liquid polyol can therefore be substituted or unsubstituted, branched or straight or cyclic, saturated or unsaturated. Non limiting examples of suitable substituents include hydroxyl groups, amines, amides, esters, ethers, alkoxylate groups (e.g., ethoxylates, propoxylates, etc.) and so forth.

Non limiting examples of suitable liquid polyols for use in the pressurized compositions of the present invention include glycerin, 1,2 propylene glycol, 1,2-butanediol; 1,2-pentanediol; 4-methyl-1,2-pentanediol; 2-methyl-1,2-pentanediol; 3,3-methyl-1,2-butanediol; 4-methyl-1,2-hexanediol; 1,2-heptanediol; 3-phenyl-1,2-propanediol; 1,2,6-hexanetriol; 1,2-hexandiol; 1,2,4-butanetriol; and combinations thereof. Other suitable liquid polyols include glycerol ethers such as glycerol isopropyl ether; glycerol propyl ether; glycerol ethyl ether; glycerol methyl ether; glycerol butyl ether; glycerol isopentyl ether; diglycerol isopropyl ether; diglycerol isobutyl ether; diglycerol; triglycerol; triglycerol isopropyl ether; and combinations thereof. Still other suitable liquid polyols include acetic acid glycerol ester; propanoic acid glycerol ester; butanoic acid glycerol ester; 3-methyl butanoic acid glycerol ester; and 3-trimethylsily-1,2-propane diol; silicone-containing 1,2-diols such as those described in U.S. Pat. No. 5,969,172 (Nye); and combinations thereof.

Carrier Liquids

The liquid aerosol antiperspirant and deodorant products of the current invention will include a carrier liquid to help deliver the antiperspirant active to skin surface in a cosmetically acceptable manner. Suitable carrier liquids for use in the aerosol antiperspirant and deodorant compositions of the present invention include any solvent that provides the consumer with a desirable cosmetic experience (e.g. feels dry, is not sticky, or irritating). Preferred carrier liquids include any silicone or silicone-containing material that is known or otherwise suitable for topical application to the skin, provided that the silicone or silicone-containing material is a liquid under ambient conditions or is otherwise in liquid form within the pressurized antiperspirant compositions of the present invention The concentration of the silicone liquid in the composition preferably ranges from about 0.1% to about 50%, more preferably from about 1% to about 25%, more preferably from about 2% to about 15%, by weight of the pressurized antiperspirant composition.

Non limiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 5 to about 6, silicon atoms. Most preferably are those that conform to the formula:

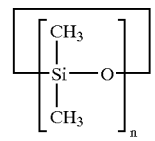

wherein n is from about 3 to about 7, preferably from about 5 to about 6, most preferably 5. These volatile cyclic silicones generally have a viscosity value of less than about 10 centistokes as measured at 25° C. Suitable volatile silicones for use herein include, but are not limited to, Cyclomethicone D-5 (commercially available from G. E. Silicones); DC 1184, Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof. Cyclopentasiloxane is most preferred among the volatile silicone liquids.

Non limiting examples of non volatile silicone liquids for use in the aerosol antiperspirant compositions of the present invention include those which conform to either of the formulas:

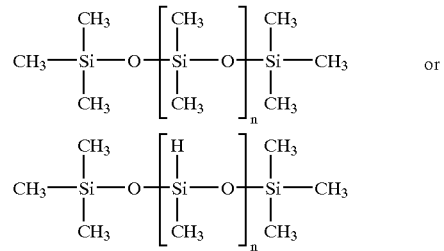

wherein n is greater than or equal to 1. These linear silicone materials will generally have viscosity values of from about 10 centistoke to about 100,000 centistoke, preferably less than about 500 centistoke, more preferably from about 10 centistoke to about 200 centistoke, even more preferably from about 10 centistoke to about 50 centistoke, as measured under ambient conditions. Non limiting examples of non-volatile, linear silicones suitable for use in the antiperspirant compositions include but are not limited to, Dow Corning 200, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G.E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available from SWS Silicones).

Other silicone liquids as carrier liquids for use in the anhydrous aerosol antiperspirant compositions of the present invention include modified or organofunctional silicone carriers such as polyalkylsiloxanes, polyalkyarylsiloxanes, cross-linked silicone elastomers, polyestersiloxanes, polyethersiloxane copolymers, polyfluorosiloxanes, polyaminosiloxanes, and combinations thereof. These modified silicone carriers are typically liquid under ambient conditions, and have a preferred viscosity of less than about 100,000 centistokes, more preferably less than about 500 centistokes, even more preferably from about 1 centistoke to about 50 centistokes, and most more preferably from about 1 centistoke to about 20 centistokes. These modified silicone carriers are generally known in the chemical arts, some examples of which are described in 1 *Cosmetics, Science and Technology* 27–104 (M. Balsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

Other non silicone based carrier liquids can also be employed in the instant invention to provide different skin feel options. Some of these may also include mono and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof. Preferably such liquid carriers are also water-immiscible liquids under ambient conditions. Other suitable water-immiscible, polar organic liquid carriers or solvents for use in combination with the 1,2-hexanediol are described in Cosmetics, Science, and Technology, Vol. 1, 27–104, edited by Balsam and Sagarin (1972); U.S. Pat. No. 4,202,879 issued to Shelton on May 13, 1980; and U.S. Pat. No. 4,816,261 issued to Luebbe et al. on Mar. 28, 1989, which descriptions are incorporated herein by reference.

Other liquid carriers for use in the instant invention include water-miscible, polar organic liquid carriers or solvents, examples of which include short chain alcohols such as ethanol and glycol solvents such as propylene glycol, hexylene glyol, dipropylene glycol, tripropylene glycol, and so forth. Other suitable similar solvents also include polyalkoxylated carriers such as polyethylene glycols, polyproylene glycols, combinations and derivatives thereof, and so forth. Non-limiting examples of polar solvents suitable for use herein are described in U.S. Pat. No. 5,429,816.

Optional liquid carriers for use in the instant invention may also include non-polar carriers such as mineral oil, petrolatum, isohexadecane, isododecane, various hydrocarbon oils such as the Isopar or Norpar series available from Exxon Corp. or Permethyl series available from Persperse, and the Soltrol series available from Phillips Chemical, and any other polar or non-polar, water-miscible, organic carrier liquid or solvent known or otherwise safe and effective for topical application to human skin.

Other optional liquid carriers for use in combination with the composition include fluorochemicals such as fluorosurfactants, fluorotelemers, and perfluoropolyethers, some examples of which are described in Cosmetics & Toiletries, Using Fluorinated Compounds in Topical Preparations, Vol. 111, pages 47–62, (October 1996) which description is incorporated herein by reference. More specific examples of such liquid carriers include, but are not limited to, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisopropyl ethers available from Dupont Performance Chemicals under the trade name Fluortress.RTM. PFPE oils, and the series fluorosurfactants from Dupont Performance Chemicals under the trade name Zonyl.RTM. Fluorosurfactants.

Having shown and described various embodiments of the present invention, further adaptations of the of the present invention as described herein can be accomplished by appropriate modifications by one of ordinary skill in the art without departing from the scope of the present invention. Several of these potential modifications and alternatives have been mentioned, and others will be apparent to those skilled in the art. For example, while exemplary embodiments of the inventive system have been discussed for illustrative purposes, it should be understood that the elements described may be constantly updated and improved by technological advances. Accordingly, the scope of the present invention should be considered in terms of the following claims and is understood not to be limited to the details of structure, operation or process steps as shown and described in the specification and drawings.

What is claimed is:

1. An underarm product and a spray package in combination, comprising:
    (a) an underarm product comprising a liquid or emulsion;
    (b) a spray package having a metered-dose valve assembly for dispensing the underarm product pressurized inside the spray package, wherein the metered-dose valve assembly is structured and configured such that a Dv(10) value of an average size of the particles in the lowest ten percent of the volume of the sprayed product is greater than 14.33 microns.

2. The underarm product and a spray package in combination according to claim 1, wherein the Dv(10) value is not less than 19.74 microns.

3. The underarm product and a spray package in combination according to claim 1, wherein the underarm product is selected from the group comprising antiperspirants and deodorants.

4. The underarm product and a spray package in combination according to claim 1, wherein the underarm product comprises a solubilized propellant.

5. The underarm product and a spray package in combination according to claim 1, wherein the underarm product comprises a non-solubilized propellant.

6. The underarm product and a spray package in combination according to claim 1, wherein the underarm product comprises an antiperspirant active selected from the group consisting of aluminum chlorohydrate, aluminum dichlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum sulfate buffered, aluminum zirconium trichlorohydrate, aluminum zirconium tretrachlorohydrate, aluminum zirconium pentachlorohydrate, aluminum zirconium octachlorohydrate, aluminum zirconium trichlorohydrdrex glycine, aluminum zirconium tretrachlorohydrex glycine, aluminum zirconium pentachlorohydrex glycine, aluminum zirconium octachlrohydrex glycine and combinations thereof.

7. The underarm product and a spray package in combination according to claim 1, wherein the underarm product comprises a deodorant active selected from the group consisting of antimicrobial, antifungal, malodor absorbing, fragrances and combinations thereof.

8. The underarm product and a spray package in combination according to claim 1, wherein the metered-dose valve has a stem orifice, a tail orifice, and a dip tube orifice, none of the orifices having an equivalent diameter less than 0.020 inches.

9. A method of increasing a spray particle size of an underarm product comprising a liquid or emulsion, the method comprising steps of (a) providing a spray package containing an underarm product comprising a liquid or emulsion pressurized inside the spray package, the spray package having a metered-dose valve assembly for dispensing the underarm product, wherein the metered-dose valve assembly is structured and configured such that a Dv(10) value of an average size of the particles in the lowest ten percent of the volume of the sprayed product is greater than 14.33 microns;

(b) actuating the metered-dose valve to spray the underarm product having the Dv(10) value of the average size of the particles in the lowest ten percent of the volume of the sprayed product is greater than 14.33 microns.

* * * * *